United States Patent
Balas et al.

(10) Patent No.: US 7,974,683 B2
(45) Date of Patent: *Jul. 5, 2011

(54) METHOD AND SYSTEM FOR CHARACTERIZATION AND MAPPING OF TISSUE LESIONS VIA LIGHT AND SPECIAL CHEMICAL AGENTS

(75) Inventors: Constantinos Balas, Athens (GR); Demetrios Pelecoudas, Patras (GR)

(73) Assignee: Forth Photonics Ltd., London (GB)

( * ) Notice: Subject to any disclaimer, the term of this patent is extended or adjusted under 35 U.S.C. 154(b) by 4 days.

This patent is subject to a terminal disclaimer.

(21) Appl. No.: 12/368,647

(22) Filed: Feb. 10, 2009

(65) Prior Publication Data
US 2009/0253991 A1 Oct. 8, 2009

Related U.S. Application Data

(63) Continuation of application No. 10/240,367, filed as application No. PCT/GR01/00017 on Mar. 28, 2001, now Pat. No. 7,515,952.

(30) Foreign Application Priority Data

Mar. 28, 2000 (GR) .................................. 000100102

(51) Int. Cl.
*A61B 1/07* (2006.01)
(52) U.S. Cl. ........................................ 600/473; 382/128
(58) Field of Classification Search .................. 600/309, 600/310, 317, 473, 475–477; 424/9.6; 359/362, 359/368; 382/128, 165; 436/172
See application file for complete search history.

(56) References Cited

U.S. PATENT DOCUMENTS

| 4,273,110 A | 6/1981 | Groux et al. |
| 5,235,984 A | 8/1993 | D'Sa |
| 5,421,339 A | 6/1995 | Ramanujam et al. |
| 5,424,543 A | 6/1995 | Dombrowski et al. |
| 5,450,857 A | 9/1995 | Garfield et al. |
| 5,647,368 A | 7/1997 | Zeng et al. |

(Continued)

FOREIGN PATENT DOCUMENTS

WO WO 92/19148 A1 11/1992

(Continued)

OTHER PUBLICATIONS

Balas et al. In vivo assessment of acetic acid-cervical tissue interaction using quantitative imaging of back-scattered light: Its potential use for the in vivo cervical cancer detection grading and mapping. SPIE vol. 3568, p. 31-37. Sep. 1998.*

(Continued)

*Primary Examiner* — Parikha S Mehta
(74) *Attorney, Agent, or Firm* — Nixon & Vanderhye P.C.

(57) ABSTRACT

A method and an apparatus for the in vivo, non-invasive, early detection of alterations and mapping of the grade of these alterations, causing in the biochemical and/or in the functional characteristics of the epithelial tissues during the development of tissue atypias, dysplasias, neoplasias and cancers is presented. The method is based, at least in part, on the simultaneous measurement of the spatial, temporal and spectral alterations in the characteristics of the light that is re-emitted from the tissue under examination, as a result of a combined tissue excitation with light and special chemical agents. The topical or systematic administration of these agents result in an evanescent contrast enhancement between normal and abnormal areas of tissue. The apparatus enables the capturing of temporally successive imaging in one or more spectral bands simultaneously.

40 Claims, 7 Drawing Sheets

U.S. PATENT DOCUMENTS

| | | | |
|---|---|---|---|
| 5,697,373 | A | 12/1997 | Richards-Kortum et al. |
| 5,791,346 | A | 8/1998 | Craine et al. |
| 5,842,995 | A | 12/1998 | Mahadevan-Jansen et al. |
| 5,920,399 | A | 7/1999 | Sandison et al. |
| 5,921,926 | A | 7/1999 | Rolland et al. |
| 5,956,144 | A | 9/1999 | Kaplan et al. |
| 5,989,184 | A | 11/1999 | Blair |
| 6,101,408 | A * | 8/2000 | Craine et al. ............. 600/425 |
| 6,134,010 | A | 10/2000 | Zavislan |
| 6,159,445 | A | 12/2000 | Klaveness et al. |
| 6,187,289 | B1 | 2/2001 | Richards-Kortum et al. |
| 6,299,860 | B1 | 10/2001 | Luiken |
| 6,332,092 | B1 | 12/2001 | Deckert et al. |
| 6,370,422 | B1 * | 4/2002 | Richards-Kortum et al. 600/478 |
| 6,411,835 | B1 | 6/2002 | Modell et al. |
| 7,515,952 | B2 * | 4/2009 | Balas et al. ............. 600/476 |
| 7,598,088 | B2 * | 10/2009 | Balas .................. 436/172 |
| 2002/0007122 | A1 * | 1/2002 | Kaufman et al. ........... 600/476 |
| 2002/0127735 | A1 | 9/2002 | Kaufman et al. |
| 2004/0111031 | A1 * | 6/2004 | Alfano et al. ............. 600/476 |

FOREIGN PATENT DOCUMENTS

| | | |
|---|---|---|
| WO | WO 98/24369 A1 | 6/1998 |
| WO | WO 99/18847 A1 | 4/1999 |
| WO | WO 01/72214 A1 | 10/2001 |

OTHER PUBLICATIONS

Andersson-Engels et al., "Preliminary Evaluation of Two Fluorescence Imaging Methods for the Detection and the Delineation of Basal Cell Carcinomas of the Skin," Lasers in Surgery and Medicine, vol. 26, pp. 76-82, 2000.

Balas et al., "In Vivo Detection and Staging of Epithelial Dysplasias and Malignancies Based on the Quantitative Assessment of Acetic Acid-Tissue Interaction Kinetics," Journal of Photochemistry and Photobiology B: Biol., vol. 53, pp. 153-157, 1999.

Glanzmann et al., "Time-Resolved Spectrofluorometer for Clinical Tissue Characterization During Endoscopy," Review of Scientific Instruments, vol. 70, No. 10, pp. 4067-4077, Oct. 1999.

Stefanaki et al., "In Vivo Detection of Human Papilloma Virus-Induced Lesions of Anogenital Area After Application of Acetic Acid: A Novel and Accurate Approach to a Trivial Method," Journal of Photochemistry and Photobiology B: Biol., vol. 65, pp. 115-121, 2001.

International Search Report mailed Jul. 13, 2001 in International Application No. PCT/GR01/00017.

Examination Report dated May 14, 2010 in Brazilian Appln. No. PI 0108944-7 with English Translation.

* cited by examiner

METHOD AND SYSTEM FOR CHARACTERIZATION AND MAPPING OF TISSUE LESIONS VIA LIGHT AND SPECIAL CHEMICAL AGENTS

RELATED APPLICATIONS

This application is a continuation of U.S. application Ser. No. 10/240,367, filed on Oct. 30, 2002, now U.S. Pat. No. 7,515,952, a 35 U.S.C. §371 National Stage of International Application Number PCT/GR01/00017 filed on Mar. 28, 2001. U.S. application Ser. No. 10/240,367 claims priority to Greek National Application Serial No. 20000100102, filed on Mar. 28, 2000 and to U.S. National application Ser. No. 09/739,089 filed on Dec. 15, 2000.

FIELD OF THE INVENTION

The present invention is directed to a method and apparatus for the in vivo, non-invasive detection and mapping of the biochemical and/or functional pathologic alterations of human tissues.

BACKGROUND OF THE INVENTION

Cancer precursor signs are the so-called pre-cancerous states, which are often curable if they are detected at an early stage. If left untreated, the pre-cancerous state can develop into invasive cancer, which can subsequently metastasize. At this stage, the possibilities of successful therapy are dramatically diminished. Consequently, the early detection and the objective identification of the severity of the pre-cancerous state are of crucial importance.

Conventional methods that utilize optical instruments are very limited in their ability to detect cancerous and pre-cancerous tissue lesions. This is due to the fact that the structural and metabolic changes, which take place during the development of the disease, do not significantly and specifically alter the spectral characteristics of the pathological tissue.

In order to obtain a more accurate diagnosis, biopsy samples are obtained from suspicious areas, which are submitted for histological examination. However, biopsies pose several problems, such as a) a risk for sampling errors associated with the visual limitations in detecting and localizing suspicious areas; b) a biopsy can alter the natural history of the intraepithelial lesion; c) mapping and monitoring of the lesion require multiple tissue sampling, which is subjected to several risks and limitations; and d) the diagnostic procedure performed with biopsy sampling and histologic evaluation is qualitative, subjective, time consuming, costly and labor intensive.

In recent years, a few methods and systems have been developed to overcome the disadvantages of the conventional diagnostic procedures. These methods can be classified into two categories: a) methods which are based on the spectral analysis of tissues in vivo, in an attempt to improve the diagnostic information, and b) methods which are based on the chemical excitation of tissues with the aid of special agents, which can interact with pathologic tissue and alter its optical characteristics selectively, thus enhancing the contrast between lesion and healthy tissue.

In the first case, the experimental use of spectroscopic techniques has been motivated by the ability of these techniques to detect alterations in the biochemical and/or the structural characteristics of tissue as the disease progresses. In particular, fluorescence spectroscopy has been extensively used in various tissues. With the aid of a light source (usually laser) of short wave length (blue-ultraviolet range), the tissue is first excited. Next, the intensity of the fluorescent light emitted by the tissue as a function of the wavelength of the light is measured.

Garfield and Glassman in No. U.S. Pat. No. 5,450,857 and Ramanajum et al. in U.S. Pat. No. 5,421,339 have presented a method based on the use of fluorescence spectroscopy for the diagnosis of cancerous and pre-cancerous lesions of the cervix. The main disadvantage of fluorescence spectroscopy is that the existing biochemical modifications associated with the progress of the disease are not manifested in a direct way as modifications in the measured fluorescence spectra. The fluorescence spectra contain limited diagnostic information for two basic reasons: a) Tissues contain non-fluorescent chromophores, such as hemoglobin. Absorption by such chromophores of the emitted light from fluorophores can result in artificial dips and peaks in the fluorescence spectra. In other words the spectra carry convoluted information for several components and therefore it is difficult assess alterations in tissue features of diagnostic importance; and b) The spectra are broad because a large number of tissue components are optically excited and contribute to the measured optical signal. As a result, the spectra do not carry specific information of the pathologic alterations and thus they are of limited diagnostic value. In short, the aforementioned fluorescent technique suffers from low sensitivity and specificity in the detection and classification of tissue lesions.

Aiming to enhance the sensitivity and specificity of the preceding method, Ramanujan et al. in the Patent No. WO 98/24369 have presented a method based on the use of neural networks for the analysis of the spectral data. This method is based on the training of a computing system with a large number of spectral patterns, which have been taken from normal and from pathologic tissues. The spectrum that is measured each time is compared with the stored spectral data, facilitating in this way the identification of the tissue pathology.

Richards-Kortum et al, in U.S. Pat. No. 5,697,373, seeking to improve the quality of the measured diagnostic information, have presented a method based on the combination of fluorescence spectroscopy and Raman scattering. The latter has the ability of providing more analytical information; however, Raman spectroscopy requires complex instrumentation and ideal experimental conditions, which substantially hinders the clinical use thereof.

It is generally known that tissues are characterized by the lack of spatial homogeneity. Consequently the spectral analysis of distributed spatial points is insufficient for the characterization of their status.

Dombrowski in U.S. Pat. No. 5,424,543, describes a multi-wavelength, imaging system, capable of capturing tissue images in several spectral bands. With the aid of such a system it is possible in general to map characteristics of diagnostic importance based on their particular spectral characteristics. However, due to the insignificance of the spectral differences between normal and pathologic tissue, which is in general the case, inspection in narrow spectral bands does not allow the highlighting of these characteristics and even more so, the identification and staging of the pathologic area.

D. R. Sandison et al., in U.S. Pat. No. 5,920,399, describe an imaging system, developed for the in vivo investigation of cells, which combines multi-band imaging and light excitation of the tissue. The system also employs a dual fiber optic bundle for transmitting light from the source to the tissue, and then from the tissue to an optical detector. These bundles are placed in contact with the tissue, and various wavelengths of excitation and imaging are combined in attempt to enhance the spectral differentiation between normal and pathologic tissue.

In U.S. Pat. No. 5,921,926, J. R. Delfyett et al. have presented a method for the diagnosis of diseases of the cervix, which is based on the combination of Spectral Interferometry and Optical Coherence Tomography (OCT). This system combines three-dimensional imaging and spectral analysis of the tissue.

Moreover, several improved versions of colpo scopes have been presented, (D. R. Craine et al., U.S. Pat. No. 5,791,346 and K. L. Blaiz U.S. Pat. No. 5,989,184) in most of which, electronic imaging systems have been integrated for image capturing, analysis of tissue images, including the quantitative assessment of lesion's size.

For the enhancement of the optical differentiation between normal and pathologic tissue, special agents are used in various fields of biomedical diagnostics, which are administered topically or systematically. Such agents include acetic acid solution, toluidine blue, and various photosensitizers (porphyrines) (S. Anderson Engels, C. Klinteb erg, K. Svanberg, S. Svanberg, In vivo fluorescence imaging for tissue diagnostics, Phys Med. Biol. 42 (1997) 815-24). The selective staining of the pathologic tissue arises from the property of these agents to interact with the altered metabolic and structural characteristics of the pathologic area. This interaction enhances progressively and reversibly the differences in the spectral characteristics of reflection and/or fluorescence between normal and pathologic tissue. Despite the fact that the selective staining of the pathologic tissue is a dynamic phenomenon, in clinical practice the intensity and the extent of the staining are assessed qualitatively and statically.

Furthermore, in several cases of early pathologic conditions, the phenomenon of temporary staining after administering the agent, is short-lasting and thus the examiner is not able to detect the alterations and even more so, to assess their intensity and extent. In other cases, the staining of the tissue progresses very slowly, resulting in patient discomfort and the creation of problems for the examiner in assessing the intensity and extent of the alterations, since they are continuously changing. The above have as direct consequence the downgrading of the diagnostic value of these diagnostic procedures. Thus, their usefulness is limited to facilitating the localization of suspected areas for obtaining biopsy samples.

Summarizing the above, the following conclusions are drawn:

a) Various conventional light dispersion spectroscopic techniques (fluorescence, elastic, non-elastic scattering, etc.) have been proposed and experimentally used for the in vivo detection of alterations in the structural characteristics of pathologic tissue. The main disadvantage of these techniques is that they provide point information, which is inadequate for the analysis of the spatially non-homogenous tissue. Multiband imaging has the potential to solve this problem by providing spectral information, of lesser resolution as a rule, in any spatial point of the area under examination. These imaging and non-imaging techniques, however, provide information of limited diagnostic value because the structural tissue alterations, which accompany the development of the disease, are not manifested as significant and characteristic alterations in the measured spectra. Consequently, the captured spectral information cannot be directly correlated with the tissue pathology, a fact that limits the clinical usefulness of these techniques.

b) The conventional (non-spectral) imaging techniques provide the capability of mapping characteristics of diagnostic importance in two or three dimensions. They are basically used for measuring morphological characteristics and as clinical documentation tools.

c) The diagnostic methods that are based on the selective staining of pathologic tissue with special agents allow the enhancement of the optical contrast between normal and pathologic tissue. Nevertheless they provide limited information for the in vivo identification and staging of the disease.

The selective interaction of pathologic tissue with the agents, which enhance the optical contrast with healthy tissue, is a dynamic phenomenon. It is therefore reasonable to suggest that the measurement and analysis of kinetic properties could provide important information for the in vivo detection, identification and staging of tissue lesions. In a previous publication, in which one of the inventors is a co-author, (C. Balas, A. Dimoka, E. Orfanoudalci, E. koumandakis, "In vivo assessment of acetic acid-cervical tissue interaction using quantitative imaging of back-scattered light: Its potential use for the in vivo cervical cancer detection grading and mapping", SPIEOptical Biopsies and Microscopic Techniques, Vol. 3568 pp. 31-37, (1998)), measurements of the alterations in the characteristics of the back-scattered light as a function of wave-length and time are presented. These alterations occur in the cervix by the topical administration of acetic acid solution. In this particular case, a general-purpose multispectral imaging system built around a tunable liquid crystal monochromator was used for measuring the variations in intensity of the back-scattered light as a function of time and wavelength at selected spatial points. It was found that the lineshapes of curves of intensity of back-scattered light versus time provide advanced information for the direct identification and staging of tissue neoplasias. Unpublished results of the same research team indicate that similar results can also be obtained with other agents, which have the property of enhancing the optical contrast between normal and pathologic tissue. Nevertheless, the experimental method employed in the published paper is characterized by quite a few disadvantages, such as: The imaging monochromator requires time for changing the imaging wavelength and as a consequence it is inappropriate for multispectral imaging and analysis of dynamic phenomena. It does not constitute a method for the mapping of the grade of the tissue lesions, as the presented curves illustrate the temporal alterations of intensity of the back-scattered light in selected points. The lack of data modeling and parametric analysis of kinetics data in any spatial point of the area of interest restricts the usefulness of the method in experimental studies and hinders its clinical implementation. The optics used for the imaging of the area of interest is of general purpose and does not comply with the special technical requirements for the clinical implementation of the method. Clinical implementation of the presented system is also hindered by the fact that it does not integrate appropriate means for ensuring the stability of the relative position between the tissue surface and image capturing module during the snapshot imaging procedure. This is very important since small movements of the patient (i.e. breathing) are always present during the examination procedure. If, after the application of the agent, micro-movements occur while an image is being recorded, then the spatial features of the captured images may not be accurate. This may substantially reduce the accuracy of the calculation of the curves in any spatial point that express the kinetics of marker-tissue interaction.

SUMMARY OF THE INVENTION

The present invention provides a method for monitoring the effects of a pathology-differentiating agent on a tissue sample. The method includes applying a pathology differentiating agent, e.g., acetic acid, on a tissue sample and measuring a spectral property, such as an emission spectrum, of the tissue sample over time, thereby monitoring the effects of a pathology differentiating agent on a tissue sample. The tissue may be a sample from: the cervix of the uterus, the vagina, the skin, the uterus, the gastrointestinal track or the respiratory track. Without intending to be limited by theory, it is believed that the pathology-differentiating agent induces transient alterations in the light scattering properties of the tissue, e.g, the abnormal epithelium.

In another aspect, the present invention features a method for the in vivo diagnosis of a tissue abnormality, e.g., a tissue atypia, a tissue dysplasia, a tissue neoplasia (such as a cervical intraepithelial neoplasia, CINI, CINII, CINIII) condylomas or cancer, in a subject. The method includes applying a pathology differentiating agent, e.g., an acetic acid solution or a combination of solutions selected from a plurality of acidic and basic solutions, to a tissue. The method further includes exposing the tissue in the subject to optical radiation, and monitoring the intensity of light emitted from the tissue over time, thereby diagnosing a tissue abnormality in a subject. The optical radiation may be broad band optical radiation, preferably polarized optical radiation.

The non-invasive methods of the present invention are useful for in vivo early detection of tissue abnormalities/alterations. The methods are also useful for mapping the grade of abnormalities/alterations in epithelial tissues during the development of tissue atypias, dysplasias, neoplasias and cancers.

In one embodiment, the tissue area of interest is illuminated with a broad band optical radiation and contacted with a pathology differentiating agent, e.g., an agent or a combination of agents which interact with pathologic tissue areas characterized by an altered biochemical composition and/or cellular functionality and provoke a transient alteration in the characteristics of the light that is re-emitted from the tissue. The light that is re-emitted from the tissue may be in the form of reflection, diffuse scattering, fluorescence or combinations or subcombinations thereof. The intensity of the light emitted from the tissue may be measured, e.g., simultaneously, in every spatial point of the tissue area of interest, at a given time point or over time (e.g., for the duration of agent-tissue interaction). A diagnosis may be made based on the quantitative assessment of the spatial distribution of alterations in the characteristics of the light re-emitted from the tissue at given time points before and after the optical and chemical excitation of the tissue. The diagnosis may also be made based on the spatial distribution of parameters calculated from kinetics curves obtained from the light re-emitted from the tissue. These curves are simultaneously measured in every spatial point of the area under examination during the optical and chemical excitation of the tissue.

In one embodiment of the invention, the step of tissue illumination comprises exposing the tissue area under analysis to optical radiation of narrower spectral width than the spectral width of the light emitted by the illumination source. In another embodiment, the step of measuring the intensity of light comprises measuring the intensity of the re-emitted light in a spectral band, the spectral width of which is narrower than the spectral width of the detector's sensitivity. In yet another embodiment, the step of measuring the intensity of light comprises measuring simultaneously the intensity of the re-emitted light in a plurality of spectral bands, the spectral widths of which are narrower than the spectral width of the detector's sensitivity.

In yet another aspect, the present invention features an apparatus for the in vivo, non-invasive early detection of tissue abnormalities/alterations and mapping of the grade of these tissue abnormalities/alterations caused in the biochemical and/or in the functional characteristics of epithelial tissues, during the development of tissue atypias, dysplasias, neoplasias and cancers. The apparatus includes optics for collecting the light re-emitted by the area under analysis, selecting magnification and focusing the image of the area. The apparatus may also include optical imaging detector(s), means for the modulation, transfer, display and capturing of the image of the tissue area of interest. In addition, the apparatus can include a computer, which has data storage, processing and analysis means, a monitor for displaying images, curves and numerical data, optics for the optical multiplication of the image of the tissue area of interest, and a light source for illuminating the area of interest. The apparatus may also include optical filters for selecting the spectral band of imaging and illumination, means for transmitting light and illuminating the area of interest, control electronics, and optionally, software for the analysis and processing of data. The software can help with the tissue image capturing and storing in specific time points and for a plurality of time points, before and after administration of the pathology-differentiating agent.

Using the foregoing apparatus, an image or a series of images may be created which express the spatial distribution of the characteristics of the kinetics of the induced alterations in the tissue's optical characteristics, before and after the administration of the agent. Pixel values of the image correspond to the spatial distribution of the alterations in the intensity of the light emitted from the tissue at given times, before and after the optical and chemical excitation of tissue. The spatial distribution of parameters may be associated with pixel gray values as a function of time. The foregoing function may be calculated from the measured and stored images and for each row of pixels with the same spatial coordinates.

In one embodiment, the step of optical filtering the imaging detector comprises an optical filter that is placed in the optical path of the rays that form the image of the tissue, for the recording of temporally successive images in a selected spectral band, the spectral width of which is narrower than the spectral width of the detector's sensitivity.

In yet another embodiment, the image multiplication optics includes light beam splitting optics that creates two identical images of the area of interest. The images are recorded by two imaging detectors, in front of which optical filters are placed. The filters are capable of transmitting light having a spectral width that is shorter than the spectral width of the detector's sensitivity, so that two groups of temporally successive images of the same tissue area are recorded simultaneously, each one corresponding to a different spectral band.

In another embodiment, the image multiplication optics include more than one beam splitter for the creation of multiple identical images of the area of interest. The images are recorded by multiple imaging detectors, in front of which optical filters are placed. The filters have different transmission characteristics and are capable of transmitting light of spectral width shorter than the spectral width of the detector's sensitivity. Thus, multiple groups of temporally successive images of the same tissue area are recorded simultaneously, each one corresponding to a different spectral band.

In a further embodiment, the image multiplication optics comprise one beam splitter for the creation of multiple identical images of the area of interest, which are recorded by multiple imaging detectors, in front of which optical filters are placed with, preferably, different transmission characteristics and capable of transmitting light of spectral width shorter than the spectral width of the detector's sensitivity, so that multiple groups of temporally successive images of the same tissue area are recorded simultaneously, each one corresponding to a different spectral band.

In yet a further embodiment, the image multiplication optics include one beam splitter for the creation of multiple identical images of the area of interest, which are recorded in different sub-areas of the same detector. Optical filters having different transmission characteristics are placed in the path of the split beams. The filters are capable of transmitting light of spectral width shorter than the spectral width of the detector's sensitivity. Multiple groups of temporally successive images of the same tissue area are recorded simultaneously in the different areas of the detector, each one corresponding to a different spectral band.

In another embodiment, the step of filtering the light source comprises an optical filter, which is placed in the optical path of an illumination light beam, and transmits light of spectral width shorter than the spectral width of sensitivity of the detector used.

In a further embodiment, the step of filtering the light source includes providing a plurality of optical filters and a mechanism for selecting the filter that is disposed in the path of the illumination light, thus enabling the tuning of the center wavelength and the spectral width of the light illuminating the tissue.

In another embodiment, the mapping of the grade of the alterations associated with the biochemical and/or functional characteristics of the tissue area of interest is based on the pixel values of one image from the group of the recorded temporally successive images of the tissue area of interest.

In a further embodiment, this mapping is based on the pixel values belonging to a plurality of images, which are members of the group of the recorded temporally successive images of the tissue area of interest.

In another embodiment, this mapping is based on numerical data derived from the pixel values belonging to a plurality of images, which are members of the group of the recorded temporally successive images of the tissue area of interest.

In a further embodiment, a pseudo-color scale, which represents with different colors the different pixel values of the image or of the images used for the mapping of abnormal tissue areas, is used for the visualization of the mapping.

In one embodiment, the image or images are used for the in vivo detection, and identification of the borders of epithelial lesions.

In another embodiment, the pixel values of the image or of the images, which are determined for the mapping of the grade of alterations in biochemical and/or functional characteristics of tissue, are used as diagnostic indices for the in vivo identification and staging of epithelial lesions.

In yet another embodiment, the image or the images can be superimposed on the color or black and white image of the same area of tissue under examination displayed on the monitor. Abnormal tissue areas are highlighted and their borders are demarcated, facilitating the selection of a representative area for taking a biopsy sample, the selective surgical removal of the abnormal area and the evaluation of the accuracy in selecting and removing the appropriate section of the tissue.

In a further embodiment, the image or the images which are determined for the mapping of the grade of alterations in biochemical and/or functional characteristics of tissue are used for the evaluation of the effectiveness of various therapeutic modalities such as radiotherapy, nuclear medicine treatments, pharmacological therapy, and chemotherapy.

In another embodiment, the optics for collecting the light re-emitted by the area under analysis includes optomechanical components employed in microscopes used in clinical diagnostic examinations, surgical microscopes, colposcopes and endoscopes.

In one embodiment of the invention directed to colposcopy applications, the apparatus may comprise a speculum, an articulated arm onto which the optical head is attached. The optical head includes a refractive objective lens, focusing optics, a mechanism for selecting the magnification, an eyepiece, a mount for attaching a camera, and an illuminator. The speculum is attached so that the central longitudinal axis of the speculum is perpendicular to the central area of the objective lens. Thus, when the speculum is inserted into the vagina and fixed in it, the relative position of the image-capturing optics and of the tissue area of interest remain unaltered, regardless of micro-movements of the cervix, which are taking place during the examination of the female subject.

In a further embodiment, the apparatus may further comprise an atomizer for delivering the agent. The atomizer is attached to the articulated arm-optical head of the apparatus and in front of the vaginal opening, where the spraying of the tissue may be controlled and synchronized with a temporally successive image capturing procedure with the aid of electronic control means.

In another embodiment of the apparatus of the invention, the image capturing detector means and image display means include a camera system. The camera system has a detector with a spatial resolution greater than 1000×1000 pixels and a monitor of at least 17 inches (diagonal), so that high magnification is ensured together with a large field of view while the image quality is maintained.

In a further embodiment directed to microscopes used in clinical diagnostic examinations, surgical microscopes and colposcopes, a system includes an articulated arm onto which the optical head is attached. The optical head includes an objective lens, focusing optics, a mechanism for selecting the magnification, an eyepiece, a mount for attaching a camera, an illuminator and two linear polarizers. One linear polarizer is disposed in the optical path of the illuminating light beam and the other in the optical path of the rays that form the image of the tissue. The polarization planes of these polarizers may be rotated. When the planes are perpendicular to each other, the contribution of the tissue's surface reflection to the formed image is eliminated.

In another embodiment directed to endoscopy, an endoscope may include optical means for transferring light from the light source to the tissue surface. The optical means may also allow the collection and transferring of rays along substantially the same axis.

The optical means also allow the focusing of the rays that form the image of the tissue. The endoscope may also include two linear polarizers. One linear polarizer is disposed in the optical path of the illuminating light beam and the other in the optical path of the rays that form the image of the tissue. The polarization planes of these polarizers may be rotated. When the planes are perpendicular to each other, the contribution of the tissue's surface reflection to the formed image is eliminated.

In another embodiment, microscopes used in clinical diagnostic examinations, surgical microscopes and colposcopes may include a reflective objective lens that replaces a refractive lens. The reflective objective lens is contracted so that a second reflection mirror is disposed in the central part of its optical front aperture. In the rear, non-reflective part of this mirror, illumination means are attached from which light is emitted toward the object. With or without illumination zooming and focusing optics, the central ray of the emitted light cone is coaxial with the central ray of the light beam that enters the imaging lens. With the aid of illumination zooming and focusing optics, which may be adjusted simultaneously and automatically with the mechanism for varying the magnification of the optical imaging system, the illuminated area and the field-of-view of the imaging system can vary simultaneously and proportionally. Any decrease in image brightness caused by increasing the magnification is compensated with the simultaneous zooming and focusing of the illumination beam.

Other features and advantages of the invention will be apparent from the following detailed description and claims.

DETAILED DESCRIPTION OF THE INVENTION

The present invention is directed to a method and system for the in vivo, noninvasive detection and mapping of the biochemical and or functional alterations of tissue, e.g., tissue within a subject. Upon selection of the appropriate pathology differentiating agent that enhances the optical contrast between normal and pathologic tissue (depending on the pathology of the tissue), this agent is administered, e.g., topically, to the tissue.

As used herein a pathology differentiating agent is any agent capable of altering the optical property of a tissue, e.g., an agent capable of altering the reflection characteristics or the fluorescence characteristics of a tissue. The pathology differentiating agent may be an acidic solution, a basic solution, a porphyrine solution or a porphyrine precursor solution. Preferred examples of a pathology differentiating agent for use in the methods of the invention include an acetic acid solution, e.g., a weak acetic acid solution, or 5-amino luvelinic acid.

Figure 1:
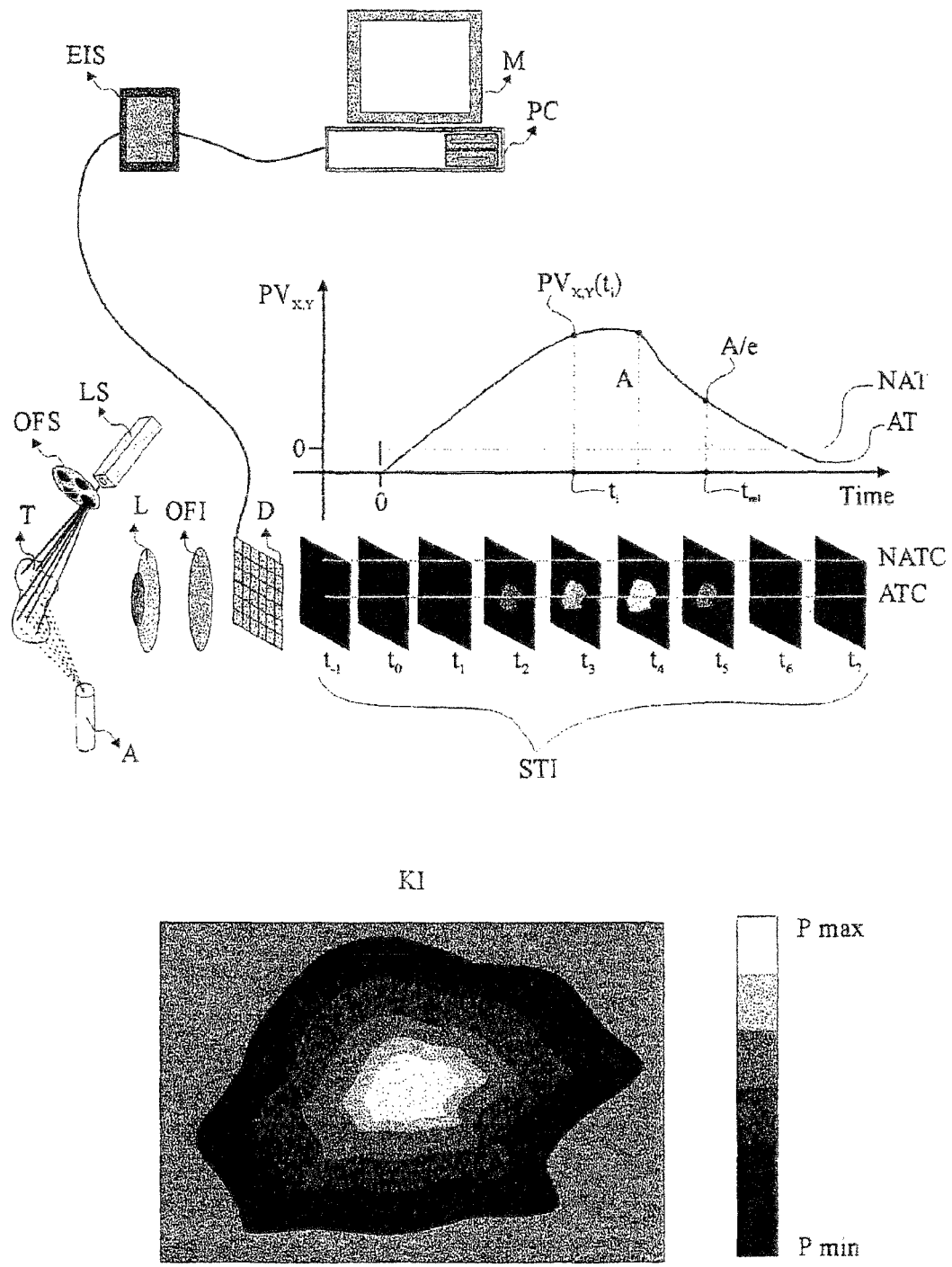
FIG. 1 is a schematic representation of the present method's basic principle.

In FIG. 1, the tissue (T), is sprayed using an atomizer (A), which contains the agent, e.g., acetic acid. At the same time, the tissue is illuminated with a source that emits light having a frequency within a specific spectral band that depends on the optical characteristics of both the agent and the tissue. The characteristics of the light emitted from the source can be controlled by choosing particular sources (LS), and optical filters (OFS). Sources of light for illuminating the tissue include light emitting diodes, and lasers.

For imaging the area of interest, light collection optics (L) may be used, which focus the image onto a two-dimensional optical detector (D). The output signal of the latter is amplified, modulated and digitized with the aid of appropriate electronics (EIS) and finally the image is displayed on a monitor (M) and stored in the data-storing means of a personal computer (PC). Between tissue (T) and detector (D), optical filters (OFI) can be interposed. The filter can be interposed for tissue (T) imaging in selected spectral bands, at which the maximum contrast is obtained between areas that are subjected to different grade of alterations in their optical characteristics after administering the appropriate agent.

Before administration of the latter, images can be obtained and used as references. After the agent has been administered, the detector (D) helps to capture images of the tissue, in successive time instances, which are then stored in the computer's data-storage means. The measuring rate is proportional to the rate at which the tissue's optical characteristics are altered, following the administration of the agent.

As used herein, an optical property, P, is a property that arises from the interaction of electromagnetic waves and a material sample, e.g., a tissue, such as a tissue within a subject. For example, the property can be the intensity of light after it interacts with matter, as manifested by an absorption, emission, or Raman spectrum. A dynamic optical property is a property that is obtained from a time-dependent optical property, P(t), and is determined from the measurement of P(t) at more than one time. For example, a dynamical optical property can be a relaxation time, or a time integral of P(t).

In FIG. 1, images of the same tissue area are schematically illustrated, which have been stored successively before and after administering the agent (STI). In these images, the black areas represent tissue areas that do not alter their optical characteristics (NAT), while the gray-white tones represent areas that alter their optical characteristics (AT), following the administration of the agent. The simultaneous capture of the intensity of the light re-emitted from every spatial point of the tissue area under analysis and in predetermined time instances, allows the calculation of the kinetics of the induced alterations.

In FIG. 1, two curves are illustrated: pixel value at position xy (Pvxy), versus time t. The curve ATC corresponds to an area where agent administration induced alterations (AT) in the tissue's optical characteristics. The curve (NATC) corresponds to an area where no alteration took place (NAT).

Each pixel, (x,y), can be associated with a pixel value, such as intensity I, which generally depends on time. For example, at time ti and pixel (x,y), the pixel value can be denoted by $PV_{xy}(ti)$. One useful dynamical spectral property, which can be obtained by measuring pixel value versus time at a particular pixel (x,y), is the relaxation time $t_{ret}(x,y)$. Letting the maximum of a PV time curve be denoted by A, then $t_{ret}(x,y)$ satisfies $PV_{xy}(t_{ret})=A/e$, where e is the base of the natural logarithm. For example, if the pixel value versus time curve can be approximated by an exponential with relaxation rate r, $PV_{x,y}(t)=A \exp(-rt)$, where $r>0$, then $t_{rel}(x,y)=1/r$.

The calculation of these parameters (P) at every spatial point of the area under analysis allows kinetic information (KI) to be obtained, with pixel values that are correlated with these parameters. These values can be represented with a scale of pseudocolors ($P_{min}$, $P_{max}$), the spatial distribution of which allows for immediate optical evaluation of the intensity and extent of the induced alterations. Depending on the correlation degree between the intensity and the extent of the induced alterations with the pathology and the stage of the tissue lesion, the measured quantitative data and the derived parameters allow the mapping, the characterization and the border-lining of the lesion. The pseudocolor image of the phenomenon's kinetics (KI), which expresses the spatial distribution of one or more parameters, can be superimposed (after being calculated) on the tissue image, which is displayed in real-time on the monitor. Using the superimposed image as a guide facilitates the identification of the lesion's boundaries, for successful surgical removal of the entire lesion, or for locating suspicious areas to obtain a biopsy sample(s). Furthermore, based on the correlation of the phenomenon's kinetics with the pathology of the tissue, the measured quantitative data and the parameters that derive from them can provide quantitative clinical indices for the in vivo staging of the lesion or of sub-areas of the latter.

In some cases it is necessary to capture the kinetics of the phenomenon in more than one spectral band. This can help in the in vivo determination of illumination and/or imaging spectral bands at which the maximum diagnostic signal is obtained. Furthermore, the simultaneous imaging in more than one spectral band can assist in minimizing the contribution of the unwanted endogenous scattering, fluorescence and reflection of the tissue, to the optical signal measured by the detector. The measured optical signal comprises the optical signal generated by the marker-tissue interaction and the light emitted from the endogenous components of the tissue. In many cases, the recorded response of the components of the tissue constitutes noise since it occludes the generated optical signal, which carries the diagnostic information. Therefore, separation of these signals, based on their particular spectral characteristics, results in the maximization of the signal-to-noise ratio and consequently in the improvement of the obtained diagnostic information.

Figure 2:
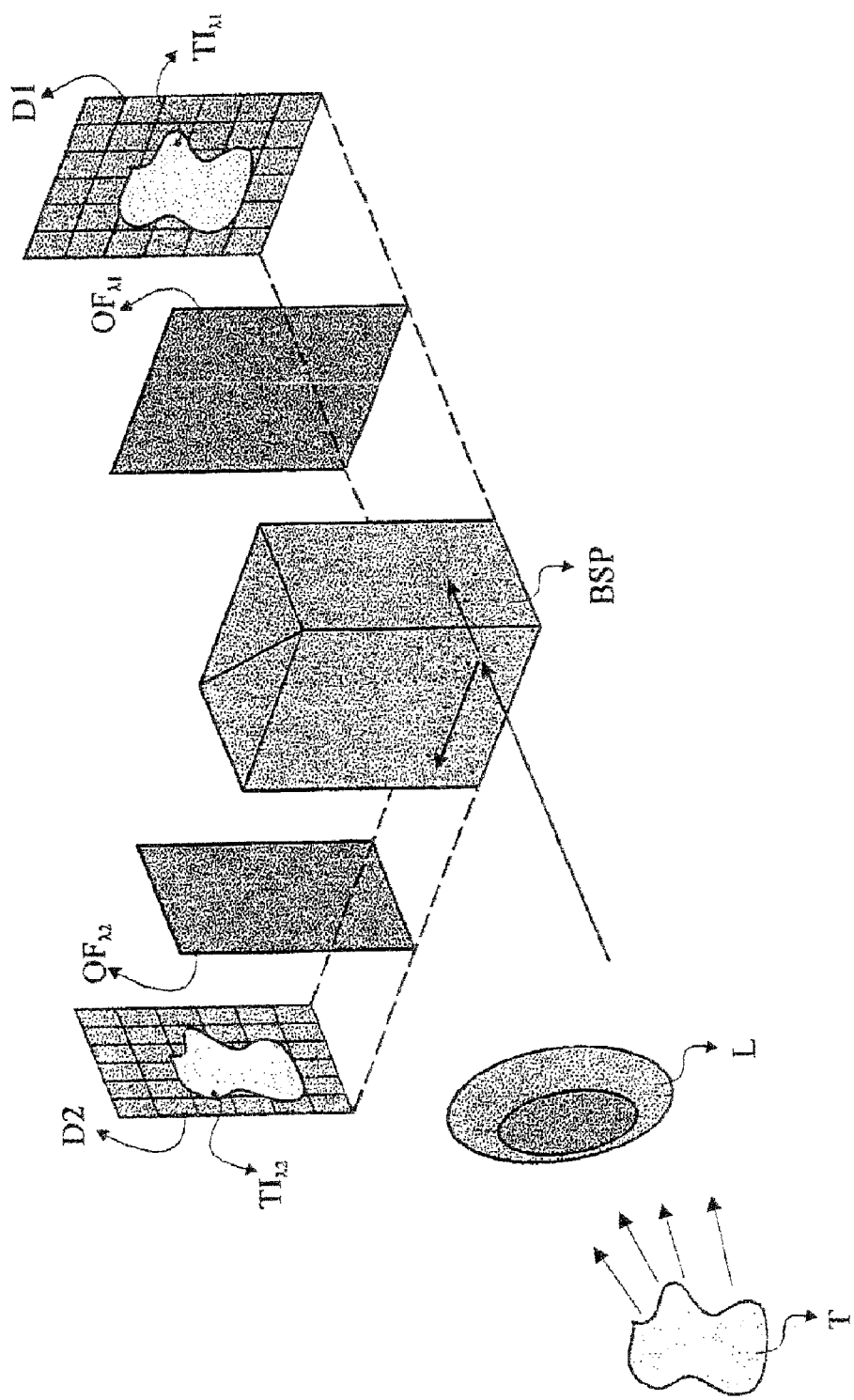
FIG. 2, illustrates an embodiment of the invention comprising a method for capturing in two spectral bands simultaneously and in any spatial point of the area under analysis, the kinetics of the alterations in the characteristics of the remitted from the tissue light, before and the after the administration of the contrast enhancing agent

FIG. 2 illustrates a method for measuring in two spectral bands simultaneously and in any spatial point of the area under analysis, the kinetics of the alterations in the characteristics of the light emitted from the tissue, before and the after the administration of the contrast enhancing agent. The light emitted from the tissue is collected and focused by the optical imaging module (L) and allowed to pass through a beam splitting (BSP) optical element. Thus, two identical images of the tissue (T) are generated, which can be captured by two detectors (D1, D2). In front of the detector, appropriate optical filters ($Of_{\lambda,1}$), ($Of_{\lambda,2}$) can be placed, so that images with different spectral characteristics are captured. Besides beam splitters, optical filters, dichroic mirrors, etc., can also be used for splitting the image of the object. The detectors (D1), (D2) are synchronized so that they capture simultaneously the corresponding spectral images of the tissue ($Ti_{\lambda,1}$), ($Ti_{\lambda,2}$) and in successive time-intervals, which are stored in the computer's data storage means. Generalizing, multiple spectral images can be captured simultaneously by combining multiple splitting elements, filters and sources.

Figure 3:
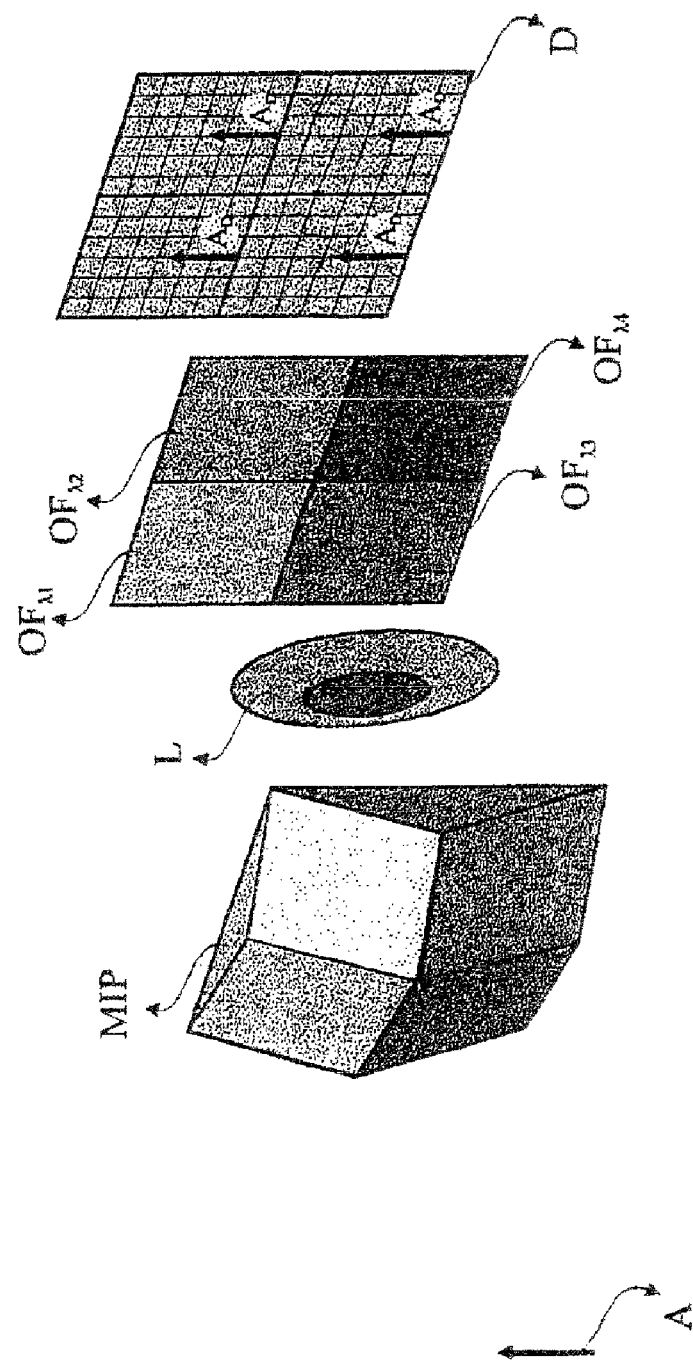
FIG. 3 illustrates another embodiment of the invention comprising a method for capturing in different spectral bands simultaneously and in any spatial point of the area under analysis, the kinetics of the alterations in the characteristics of the remitted from the tissue light, before and the after the administration of the contrast enhancing agent.

FIG. 3 illustrates another method for capturing in different spectral bands simultaneously and in any spatial point of the area under analysis, the kinetics of the alterations in the characteristics of the light emitted from the tissue, before and the after the administration of the contrast enhancing agent. With the aid of a special prism (MIP) and imaging optics, it is possible to form multiple copies of the same image onto the surface of the same detector (D). Various optical filters ($OF_{\lambda,1}$), ($OF_{\lambda,2}$), ($OF_{\lambda,3}$), and ($OF_{\lambda,4}$), can be interposed along the length of the optical path of the rays that form the copies of the object's image, so that the multiple images correspond to different spectral areas.

For the clinical use of the methods of the invention, the different implementations of imaging described above can be integrated to conventional optical imaging diagnostic devises. Such devises are the various medical microscopes, colposcopes and endoscopes, which are routinely used for the in vivo diagnostic inspection of tissues. Imaging of internal tissues of the human body requires in most cases the illumination and imaging rays to travel along the same optical path, through the cavities of the body. As a result, in the common optical diagnostic devices the tissue's surface reflection contributes substantially to the formed image. This limits the imaging information for the subsurface characteristics, which is in general of great diagnostic importance. This problem becomes especially serious in epithelial tissues such as the cervix, larynx, and oral cavity, which are covered by fluids such as mucus and saliva. Surface reflection also obstructs the detection and the measurement of the alterations in the tissue's optical properties, induced after the administration of agents, which enhance the optical contrast between normal and pathologic tissue. More specifically, when an agent alters selectively the scattering characteristics of the pathologic tissue, the strong surface reflection that takes place in both pathologic (agent responsive) and normal (agent non responsive) tissue areas, occludes the diagnostic signal that originates from the interaction of the agent with the subsurface features of the tissue. In other words, surface reflection constitutes optical noise in the diagnostic signal degrading substantially the perceived contrast between agent responsive and agent non-responsive tissue areas.

Figure 4:
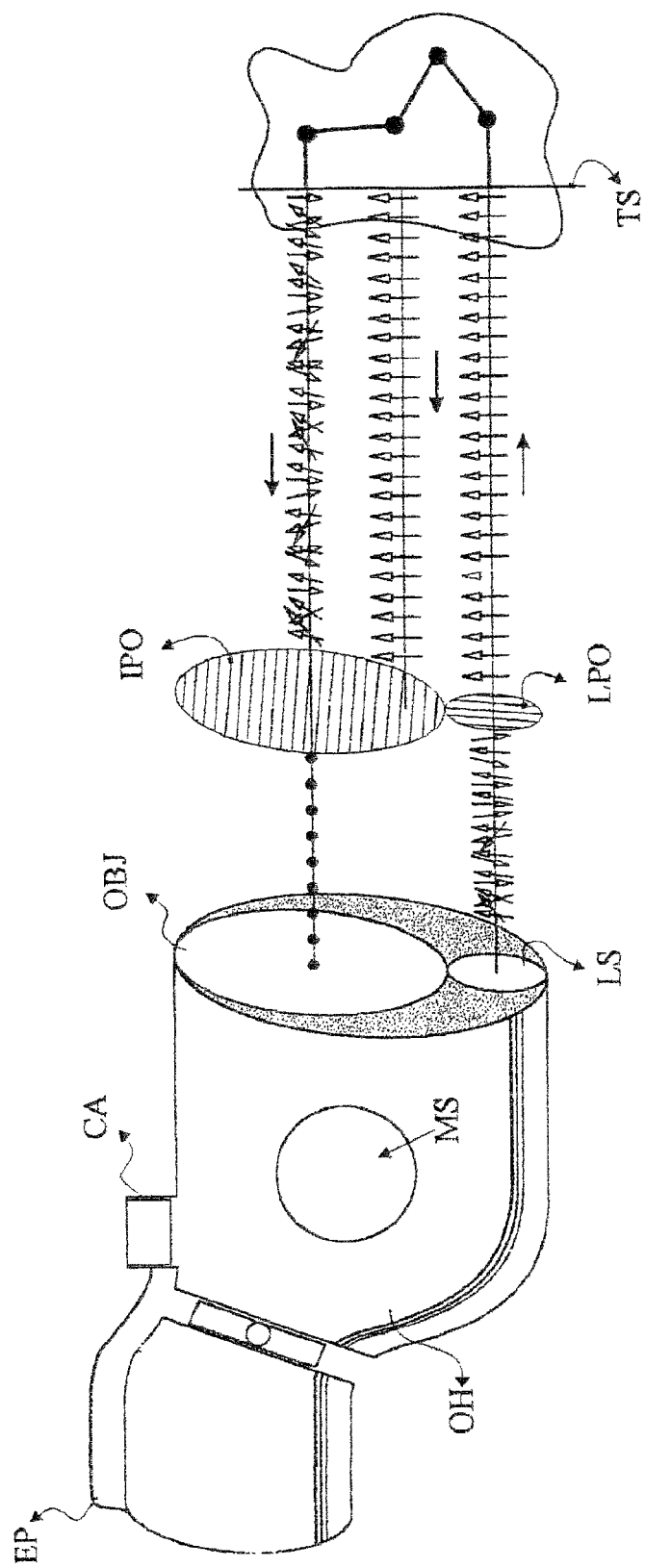
FIG. 4 illustrates a schematic diagram of a medical microscope comprising a light source (LS), a magnification selection mechanism (MS), an eyepiece (EP) and a mount for attaching the image capturing module (CA), (detector(s), readout electronics etc).

For accurate diagnoses using the aforementioned imaging devices, appropriate optics can be used to eliminate noise arising from surface reflection. FIG. 4 illustrates a schematic diagram of a medical microscope that includes a light source (LS), a magnification selection mechanism (MS), an eyepiece (EP) and a mount for attaching the image capturing module (CA), (detector(s), readout electronics etc). To eliminate surface reflection, a pair of linear polarizers is employed. Light from the source passes through a linear polarizer (LPO) with the resulting linearly polarized light (LS) then impinging on the tissue. The surface reflected light (TS) has the same polarization plane as the incident light (Fresnel reflection). By placing another linear polarizer (IPO), oriented at a right angle with respect to the first, in the path of the light emitted from the tissue, the contribution of the surface reflected light is eliminated. The light that is not surface reflected enters the tissue, where due to multiple scattering, light polarization is randomized. Thus, a portion of the re-emitted light passes through the imaging polarization optics, carrying improved information for the subsurface features.

Figure 5:
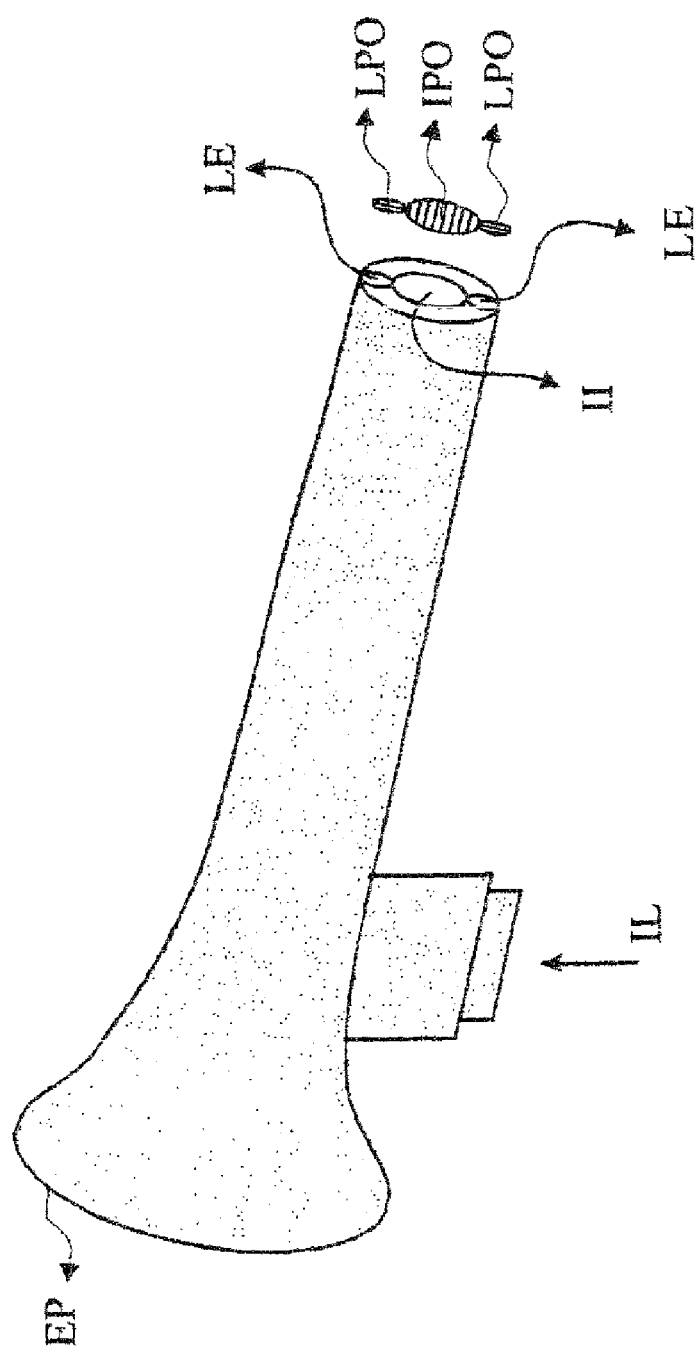
FIG. 5 illustrates an endoscope comprising an eyepiece (EP), which can be adapted to an electronic imaging system, optical fibers or crystals for the transmission of both illumination and image rays, optics for the linear polarization of light, one interposed to the optical path of the illumination rays (LE) and one to the path of the ray that form the optical image of the tissue (II).

FIG. 5 illustrates an endoscope that includes an eyepiece (EP), which can be adapted to an electronic imaging system, and optical fibers or crystals for the transmission of both illumination and image rays. The endoscope also includes a first linear polarizer (LPO), disposed in the optical path of the illumination rays (LE), and a second polarizer (IPO), oriented at right angles to the first, disposed in the path of the light emitted by the tissue (II). The polarizer (LPO) can be disposed as shown in the figure, or, alternatively, where the light enters the endoscope (IL). In the latter case, the endoscope has to be constructed using polarization preserving crystals or fiber optics for transferring the light. If polarization preserving light transmission media are used, then the polarizers for the imaging rays can be disposed in their path, in front or in back of the eyepiece (EP).

A problem for the effective clinical implementation of the method described above involves the micro-movements of the patient, which are present during the snapshot imaging of the same tissue area. This problem is eliminated when the patient is under anesthesia (open surgery). In most cases, however, the movements of the tissue relative to the image capturing module, occurring during the successive image capturing time-course, result in image pixels, with the same image coordinates, which do not correspond to exactly the same spatial point x,y of the tissue area under examination.

This problem is typically encountered in colposcopy. A method for eliminating the influence to the measured temporal data of the relative movements between tissue and image capturing module is presented below.

Figure 6:
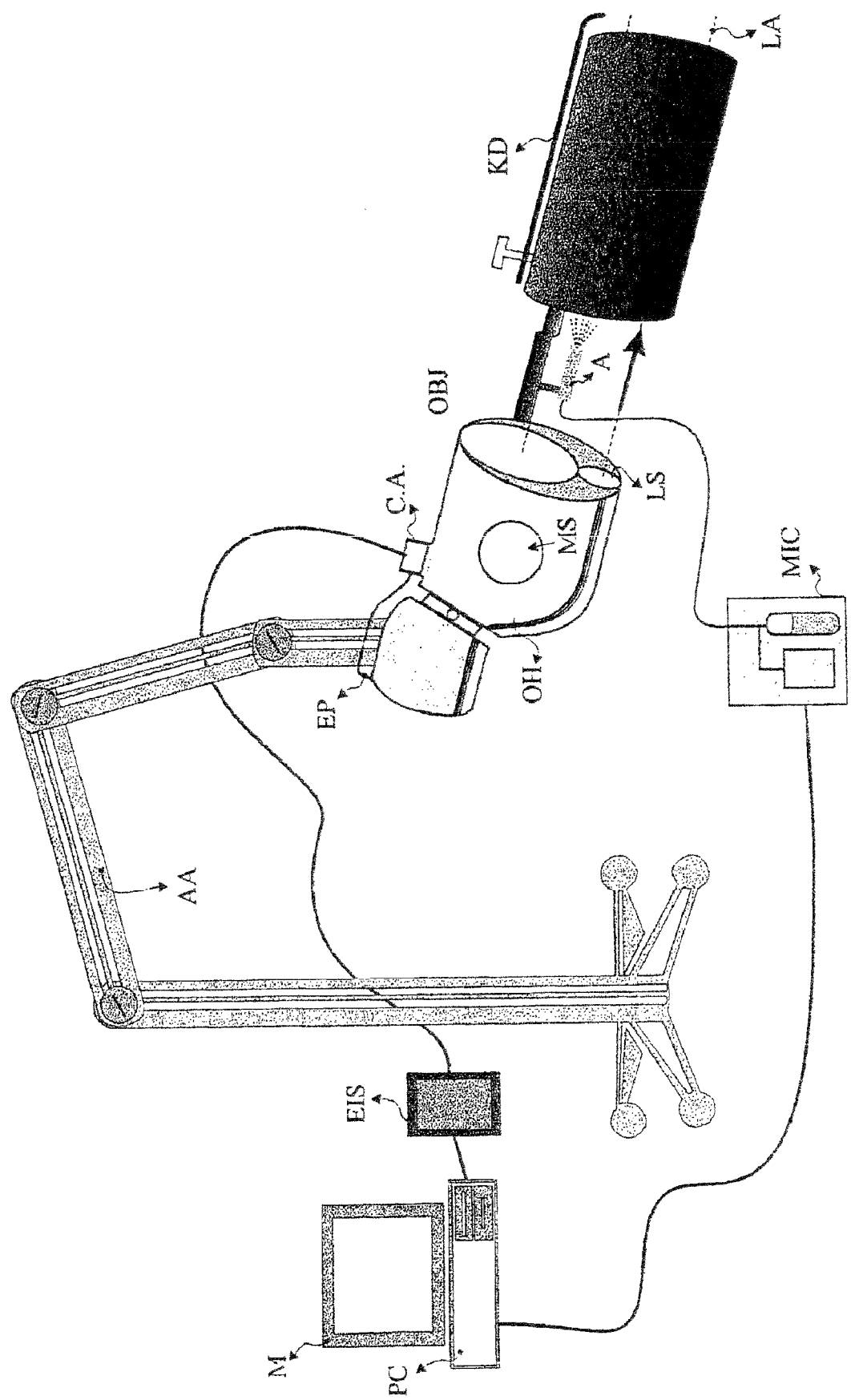
FIG. 6 depicts a colposcopic apparatus comprising an articulated arm (AA), onto which the optical head (OH) is affixed, which includes a light source (LS), an objective lens (0133), an eye-piece (EP) and optics for selecting the magnification (MS).

A colposcopic apparatus, illustrated in FIG. 6, includes an articulated arm (AA), onto which the optical head (OH) is affixed. The head (OH) includes a light source (LS), an objective lens (OBJ), an eyepiece (EP) and optics for selecting the magnification (MS). The image-capturing module is attached to the optical head (OH), through an opto-mechanical adapter. A speculum (K.D), which is used to open-up the vaginal canal for the visualization of the cervix, is connected mechanically to the optical head (OH), so that its longitudinal symmetry axis (LA) is perpendicular to the central area of the objective lens (OBJ). The speculum enters the vagina and its blades are opened up compressing the side walls of the vagina. The speculum (I(D), being mechanically connected with the optical head (OH), transfers any micromovement of the patient to the optical head (OH), which, being mounted on an articulated arm (AA), follows these movements. Thus the relative position between tissue and optical head remains almost constant.

An important issue that must also be addressed for the successful clinical implementation of the diagnostic method described herein is the synchronization of the application of the pathology differentiating agent with the initiation of the snapshot imaging procedure. FIG. 6, illustrates an atomizer (A) attached to the optical head of the microscope. The unit (MIC) is comprised of electronics for controlling the agent sprayer and it can incorporate also the container for storing the agent. When the unit (MIC) receives the proper command from the computer, it sprays a predetermined amount of the agent onto the tissue surface, while the same or another command initiates the snapshot image capturing procedure.

The diagnostic examination of non-directly accessible tissues located in cavities of the human body (ear, cervix, oral cavity, esophagus, colon, stomach) is performed with the aid of common clinical microscopes. In these devices, the illumination-imaging rays are near co-axial. More specifically, the line perpendicular to the exit point of light into the air, and the line perpendicular to the objective lens, form an angle of a few degrees. As a result, these microscopes operate at a specific distance from the subject (working distance), where the illuminated tissue area coincides with the field-of view of the imaging system. These microscopes are found to be inappropriate in cases where tissue imaging through human body cavities of small diameter and at short working distances is required. These technical limitations hinder the successful clinical implementation of the method described herein. As discussed above, elimination of surface reflection results in a substantial improvement of the diagnostic information obtained from the quantitative assessment of marker-tissue interaction kinetics. If a common clinical microscope is employed as the optical imaging module, then as a result of the above-mentioned illumination-imaging geometry, multiple reflections occur in the walls of the cavity before the light reaches the tissue under analysis. Multiple reflections are more numerous in colposcopy because of the highly reflective blades of the speculum, which is inserted into the vagina to facilitate the inspection of the cervix.

If the illuminator of the imaging apparatus emits linearly polarized light, the multiple reflections randomize the polarization plane of the incident light. As discussed above, if the light impinging on the tissue is not linearly polarized, then the elimination of the contribution from the surface reflection to the image can not be effective.

Figure 7:
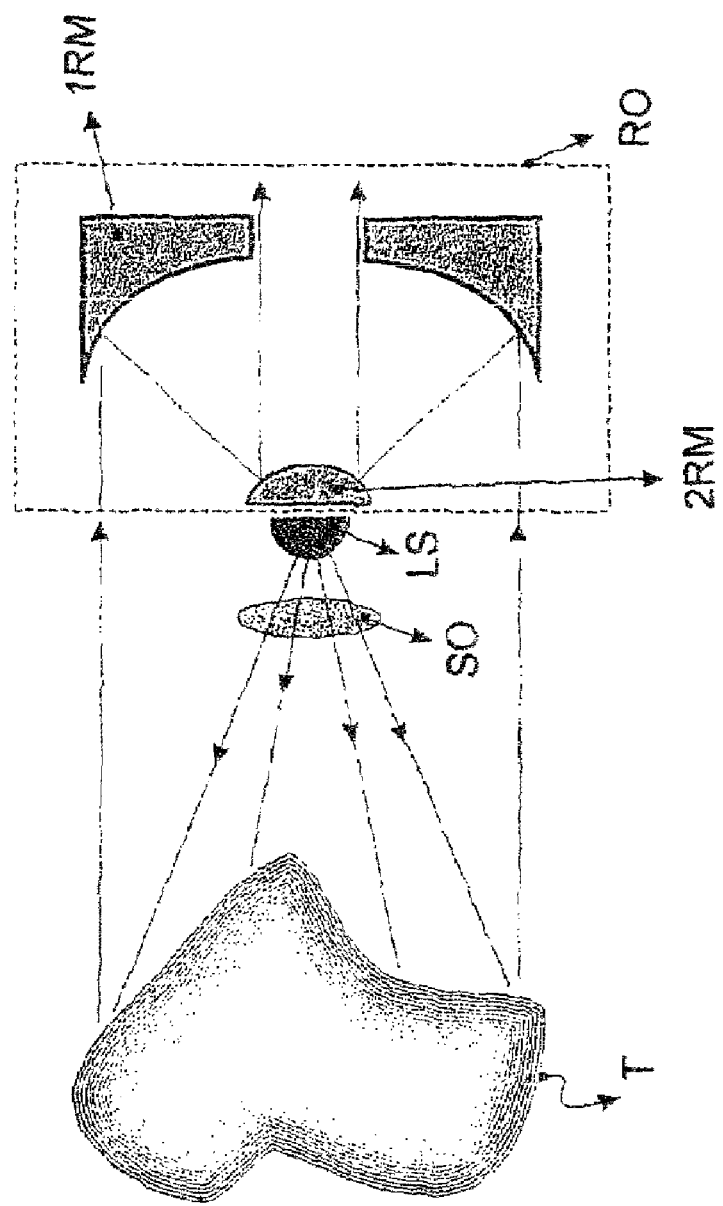
FIG. 7 illustrates an optical imaging apparatus which comprises a light source located at the central part of its front-aperture.

FIG. 7 illustrates an optical imaging apparatus that includes a light source located at the central part of its front-aperture. With this arrangement, the central ray of the emitted light cone is coaxial with the central ray of the light beam that enters the imaging apparatus. This enables illumination rays to directly reach the tissue surface under examination before multiple reflections occur with the wall of the cavity or speculum. A reflective-objective lens is used, which includes a first reflection (1RM) and a second reflection (2RM) mirror. A light source (LS) is disposed at the rear of the second reflection mirror (2RM), together with, if required, optics for light beam manipulation such as zooming and focusing (SO). The reflective-objective lens (RO), by replacing the common refractive-objective used in conventional microscopes, provides imaging capability in cavities of small diameter with the freedom of choosing the working distance. The zooming and focusing optics of the light beam can be adjusted simultaneously with the mechanism for varying the magnification of the optical imaging system so that the illumination area and the field-of-view of the imaging system vary simultaneously and proportionally. Thus, image brightness is preserved regardless of the magnification level of the lens. The imaging-illumination geometry embodied in this optical imaging apparatus, along with the light beam manipulation options, helps to eliminate the surface reflection contribution to the image and consequently helps to efficiently implement the method described herein.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for monitoring the effects of a pathology differentiating agent on a tissue sample, the method comprising:
 (a) applying a pathology differentiating agent to an examination area of a tissue sample;
 (b) exposing the examination area of the tissue sample to optical radiation;
 (c) measuring the intensity of scattered light re-emitted from the examination area of the tissue sample over time, within a life-time of transient optical effects provoked by the pathology differentiating agent following its administration to the examination area of the tissue sample;

(d) computing a curve for each spatial point of the examination area of the tissue sample of the intensity of scattered light re-emitted from the examination area of the tissue sample versus time;

(e) calculating from each curve at least one dynamic optical parameter, and (f) creating an artificial image expressing the spatial distribution of the at least one dynamic optical parameter with the pixel values of the artificial image corresponding to each spatial point of the examination area of the tissue sample.

2. The method of claim 1, wherein said dynamic optical parameter is one of a maximum of the curve of the intensity of scattered light re-emitted from the examination area of the tissue sample versus time, a time to maximum, a relaxation time, or an integral of a function P(t), where P is the intensity of scattered light re-emitted from the examination area of the tissue sample and t is time.

3. The method of claim 1, wherein the examination area of the tissue sample is exposed to broadband optical radiation.

4. The method of claim 1, wherein the examination area of the tissue sample is exposed to optical radiation of narrower spectral width than a width of the emission spectral range of optical radiation emitted by the original illumination optical radiation source.

5. The method of claim 1, wherein the intensity of the scattered light re-emitted from the examination area of the tissue sample is simultaneously measured in every spatial point of the examination area of the tissue sample.

6. The method of claim 5, wherein the intensity of the scattered light re-emitted from the examination area of the tissue sample is simultaneously measured in more than one spectral band.

7. The method of claim 5, wherein measurement of the intensity of the scattered light re-emitted from the examination area of the tissue sample is obtained by capturing of images recorded in successive time points and having pixels each associated with an intensity of the examined tissue area of interest, at a given time instance.

8. The method of claim 7, wherein the images recorded in successive time points are one or more spectral images captured simultaneously in each time instance.

9. The method of claim 7, wherein the application of the pathology differentiating agent to the examination area of the tissue sample and the initiation of the imaging procedure are synchronized.

10. The method of claim 1, wherein the pathology differentiating agent is selected from a group of acidic and basic solutions.

11. The method of claim 10, wherein the group of acidic and basic solutions includes an acetic acid solution.

12. The method of claim 1, wherein the artificial image of the examination area of the tissue sample expressing the spatial distribution of the at least one dynamic optical parameter with the pixel values of the artificial image corresponding to each spatial point of the examination area of the tissue sample is represented by a scale of pseudo colors.

13. The method of claim 12, wherein said pseudo color represented artificial image is superimposed on a real image of the examination area of the tissue sample.

14. The method of claim 1, wherein the examination area of the tissue sample is exposed to polarized light.

15. The method of claim 14, further comprising polarizing light re-emitted from the examination area of the tissue sample in a direction perpendicular to the direction of polarization of the light to which the examination area of the tissue sample was originally exposed.

16. An imaging apparatus for monitoring the effects of a pathology differentiating agent on a tissue sample comprising:

(a) an applicator configured to apply a pathology differentiating agent to an examination area of a tissue sample, (b) a light source configured to expose the examination area of the tissue sample to optical radiation;

(c) optics configured to collect light re-emitted by the examination area of the tissue sample, under analysis for magnification and focusing an image of the examination area of the tissue sample;

(d) an optical imaging detector;

(e) means for modulating, transferring, displaying and capturing of the image of the examination area of the tissue sample;

(f) at least one computer configured for data storage, processing and analysis, the computer including software configured to compute a curve, for each spatial point of the examination area of the tissue sample, of the intensity of scattered light re-emitted from the examination area of the tissue sample versus time, within the life-time of the transient optical effects provoked by the pathology differentiating agent following its administration to the examination area of the tissue sample;

wherein the software is further configured to calculate, from each curve, at least one dynamic optical parameter, and to create an artificial image expressing the spatial distribution of the at least one dynamic optical parameter with the pixel values of the artificial image corresponding to each spatial point of the examination area of the tissue sample.

17. The imaging apparatus of claim 16, further comprising a monitor for displaying the image.

18. The imaging apparatus of claim 16, wherein said dynamic optical parameter is one of a maximum of the curve of the intensity of scattered light re-emitted from the examination area of the tissue sample versus time, a relaxation time, or a integral of a function P(t), where P is the intensity of scattered light re-emitted from the examination area of the tissue sample and t is time.

19. The imaging apparatus of claim 16, wherein the light source produces broadband optical radiation.

20. The imaging apparatus of claim 16, further comprising optical filters for selecting the spectral band of imaging and illumination.

21. The imaging apparatus of claim 20, further comprising an optical filter placed in the path of the optical radiation that forms an image of the examination area of the tissue for the recording of temporally successive images in a selected spectral band, the spectral width of which is narrower than the spectral width of the optical imaging detector's sensitivity.

22. The imaging apparatus of claim 16, wherein the intensity of scattered light re-emitted from the examination area of the tissue sample is simultaneously measured in every spatial point of the examination area of the tissue sample.

23. The imaging apparatus of claim 22, wherein the intensity of scattered light is simultaneously measured in more than one spectral band.

24. The imaging apparatus of claim 22, wherein measurement of the intensity of scattered light is obtained by capturing of images recorded in successive time points and having pixels each associated with an intensity of the examined tissue area of interest, at a given time instance.

25. The imaging apparatus of claim 24 wherein said images are one or more spectral images captured simultaneously in each time instance.

26. The imaging apparatus of claim 16, wherein the image of the examination area of the tissue sample expressing the spatial distribution of the at least one dynamic optical parameter with the pixel values of the image corresponding to each spatial point of the examination area of the tissue sample is represented by a scale of pseudo colors.

27. The imaging apparatus of claim 26, wherein the pseudo color represented artificial image is superimposed on a real image of the examination area of the tissue sample.

28. The imaging apparatus of claim 16, further comprising a linear polarizer for polarizing the light emitted from the light source.

29. The imaging apparatus of claim 28, further comprising another linear polarizer for polarizing light re-emitted from the examination area of the tissue sample in a direction perpendicular to the direction of polarization of the light to which the examination area of the tissue sample was originally exposed.

30. The imaging apparatus of claim 16, wherein the optics for collecting light re-emitted by the examination area of the tissue sample for magnification and focusing an image of the examination area of the tissue sample include optomechanical components employed in microscopes used in clinical diagnostic examinations, surgical microscopes, colposcopes and endoscopes.

31. The imaging apparatus of claim 16, wherein the optical imaging detector is a two dimensional optical detector.

32. The imaging apparatus of claim 30 used for colposcopy applications, and comprising an articulated arm onto which an optical head is attached, the optical head comprising the light source for illuminating the tissue sample with optical radiation, optics for collecting light re-emitted by the tissue under analysis for magnification and focusing an image of the examination area of the tissue and the optical imaging detector and including a refractive objective lens, focusing optics, a mechanism for selecting magnification, an eyepiece, a mount for attaching a camera and an illuminator.

33. The imaging apparatus of claim 32, further comprising a speculum.

34. The imaging apparatus of claim 33, wherein the speculum is mechanically connected to the optical head so that its longitudinal axis is perpendicular to the central area of the objective lens, thus ensuring the relative position between the examination area of the tissue sample and the optical head remains almost constant.

35. The imaging apparatus of claim 32, wherein the applicator for administering a pathology differentiating agent to the examination area of the tissue sample is an atomizer attached to the optical head.

36. The imaging apparatus of claim 16, further comprising electronic control means for synchronizing the application of the pathology differentiating agent to the examination area of the tissue sample and the initiation of the imaging procedure.

37. The imaging apparatus of claim 16, wherein the applicator contains an acetic acid solution.

38. The imaging apparatus of claim 16, including optics for the optical multiplication of the image of the examination area of the tissue sample.

39. The imaging apparatus of claim 38, wherein the optics for the optical multiplication of the image of the examination area of the tissue sample include light splitting optics that create two identical images of the area of interest.

40. The imaging apparatus of claim 38, wherein the optics for the optical multiplication of the image of the examination area of the tissue sample include more than one beam splitter that create multiple identical images of the area of interest.

\* \* \* \* \*